United States Patent
Orava et al.

(10) Patent No.: US 11,191,698 B2
(45) Date of Patent: Dec. 7, 2021

(54) APPARATUS AND METHOD FOR PROCESSING PLATELET RICH FIBRIN

(71) Applicant: ENSO DISCOVERIES, LLC, Manhattan, KS (US)

(72) Inventors: James Corey Orava, Manchester, VT (US); Patrick Farley, Manhattan, KS (US)

(*) Notice: Subject to any disclaimer, the term of this patent is extended or adjusted under 35 U.S.C. 154(b) by 665 days.

(21) Appl. No.: 15/803,284

(22) Filed: Nov. 3, 2017

(65) Prior Publication Data

US 2019/0133881 A1     May 9, 2019

(51) Int. Cl.
| | |
|---|---|
| *B01L 3/00* | (2006.01) |
| *A61J 1/14* | (2006.01) |
| *A61M 1/36* | (2006.01) |
| *A61M 1/02* | (2006.01) |
| *A61L 15/32* | (2006.01) |
| *C12M 1/33* | (2006.01) |
| *A61K 35/19* | (2015.01) |

(52) U.S. Cl.
CPC .................. *A61J 1/14* (2013.01); *A61L 15/32* (2013.01); *A61M 1/0259* (2013.01); *A61M 1/3693* (2013.01); *A61K 35/19* (2013.01); *A61M 2202/0415* (2013.01); *A61M 2202/0423* (2013.01); *A61M 2202/0427* (2013.01); *C12M 45/02* (2013.01)

(58) Field of Classification Search
CPC ........... B01L 3/5085; B01L 2300/0829; B01L 2200/025
USPC .................................................. 422/551–554
See application file for complete search history.

(56) References Cited

U.S. PATENT DOCUMENTS 5,585,275 A * 12/1996 Hudson .................. B01D 61/18
422/129

FOREIGN PATENT DOCUMENTS

WO     2017070758     5/2017

OTHER PUBLICATIONS

Patent Cooperation Treaty, International Search Report for PCT/US2018/05888, 3pgs, dated Feb. 25, 2019.
Osung Catalogue 2017·2018, retrieved from www.osung.co.kr/company/osung_catalogue2017_en.pdf Feb. 27, 2017.

* cited by examiner

*Primary Examiner* — Natalia Levkovich
(74) *Attorney, Agent, or Firm* — Patent Law Agency, LLC; Peter Ganjian

(57) ABSTRACT

A tray for processing platelet rich fibrin includes a base having at least one alignment structure, a screen attachment having at least one alignment structure for engagement with the base, and a lid having at least one alignment structure for engagement with the base and the screen attachment. The screen attachment includes a screen offset between the top and bottom surface of the screen. When the screen attachment is placed on the base with the top surface facing upward, the lid is configured to compress a fibrin clot placed on the screen to a first thickness, and when the screen attachment is placed on the base with the bottom surface facing upward the lid is configured to compress a fibrin clot placed on the screen to a second thickness different from the first thickness.

13 Claims, 13 Drawing Sheets

APPARATUS AND METHOD FOR PROCESSING PLATELET RICH FIBRIN

FIELD

The present disclosure generally relates to medical apparatus and procedures, and more particularly to an apparatus and method for processing platelet rich fibrin for use in medical procedures.

BACKGROUND

Thin compressed layers of platelet rich fibrin are used in medical procedures, such as in suturing and wound care. The use of platelet rich fibrin facilitates and speeds healing of a wound. Typically, first a sample of blood is centrifuged to separate red blood cells from the serum. The sample is permitted time for a clot to form. The fibrin clot is removed from the sample and placed on a screen to be compressed. After the clot is removed, a variable amount of serum may remain. The serum can be used in a medical procedure as well, such as by injection into a wound to aid healing. During compression of the removed clot, serum is expressed from the clot, until what remains is a thin layer of platelet rich fibrin. The serum expressed during compression is often wasted. The compressed platelet rich fibrin can then be used in a medical procedure, such as by suturing the platelet rich fibrin onto a wound. A fibrin clot retrieved after centrifuging can be quite thick, and it may be difficult to compress the clot into a usable thickness. Furthermore, it may be desirable to utilize platelet rich fibrins of differing thicknesses, or to combine multiple platelet rich fibrins, depending on the application.

SUMMARY

Among the various aspects of the present disclosure is the provision of an apparatus or assembly for processing platelet rich fibrin as substantially shown and described.

Briefly, therefore, one aspect of the disclosure is directed to a tray for processing platelet rich fibrin. The tray includes a base having top, bottom, left, right, front, and back surfaces and at least one alignment structure. A screen attachment has a top surface, a bottom surface, and a screen inset between the top and bottom surfaces. The screen attachment has at least one alignment structure configured for engagement with the at least one alignment structure of the base to align the screen attachment with the base. A lid has a top surface, a bottom surface, and at least one alignment structure configured for engagement with the at least one alignment structure of the base to align the lid with the screen attachment and the base. The screen is spaced a first distance below the top surface of the screen attachment and spaced a second distance different from the first distance above the bottom surface of the screen attachment, such that when the screen attachment is placed on the base with the top surface facing upward the lid is configured to compress a fibrin clot placed on the screen to a first thickness, and when the screen attachment is placed on the base with the bottom surface facing upward the lid is configured to compress a fibrin clot placed on the screen to a second thickness different from the first thickness.

Another aspect of the disclosure is directed to a tray for processing platelet rich fibrin. The tray includes a base having top, bottom, left, right, front, and back surfaces, and at least one alignment structure. The base includes an interior receptacle and an opening in the top surface providing access to the interior receptacle. A screen attachment has a top surface, a bottom surface, and a screen. The screen attachment has at least one alignment structure configured for engagement with the at least one alignment structure of the base to align the screen attachment with the base such that the screen overlies the opening of the base. A lid has a top surface, a bottom surface, and at least one alignment structure configured for engagement with the at least one alignment structure of the base to align the lid with the screen attachment and the base. The front surface of the base includes a front access opening. The interior receptacle is tapered and slanted toward the front access opening such that liquid flowing through the screen and into the interior receptacle is directed toward the front access opening for removal from the base through the front access opening.

Another aspect of the disclosure is directed to a method of processing platelet rich fibrin including placing a fibrin clot on a tray. The tray includes a base having top, bottom, left, right, front, and back surfaces. The base includes at least one alignment structure, an interior receptacle, and an opening in the top surface providing access to the interior receptacle. The front surface of the base includes a front access opening, the interior receptacle being tapered and slanted toward the front access opening. A screen attachment has a top surface, a bottom surface, and a screen inset between the top and bottom surfaces. The screen attachment has at least one alignment structure configured for engagement with the at least one alignment structure of the base to align the screen attachment with the base such that the screen overlies the opening of the base. The screen is spaced a first distance below the top surface of the screen attachment and spaced a second distance different from the first distance above the bottom surface of the screen attachment. A lid has a top surface, a bottom surface, and at least one alignment structure configured for engagement with the at least one alignment structure of the base to align the lid with the screen attachment and the base. Placing the fibrin clot on the tray includes placing the fibrin clot on the screen of the screen attachment, the screen attachment being attached to the base in a first orientation such that the top surface of the screen attachment is facing upward. The lid is pressed downward to compress the fibrin clot, such that serum is expressed from the fibrin clot, flows through the screen and into the interior receptacle, and is directed toward the front access opening, and the fibrin clot is compressed to a first uniform thickness equal to the first distance. The screen attachment is flipped to a second orientation such that the bottom surface of the screen attachment is facing upward. The lid is pressed downward to further compress the fibrin clot to a second uniform thickness equal to the second distance and smaller than the first uniform thickness.

Other objects and features will be in part apparent and in part pointed out hereinafter.

BRIEF DESCRIPTION OF THE DRAWINGS

These and other features, aspects and advantages of the disclosure will become more fully apparent from the following detailed description, appended claims, and accompanying drawings, wherein the drawings illustrate features in accordance with exemplary aspects of the disclosure, and wherein:

Like reference numerals indicate corresponding parts throughout the several views of the drawings.

DETAILED DESCRIPTION

Figure 1:
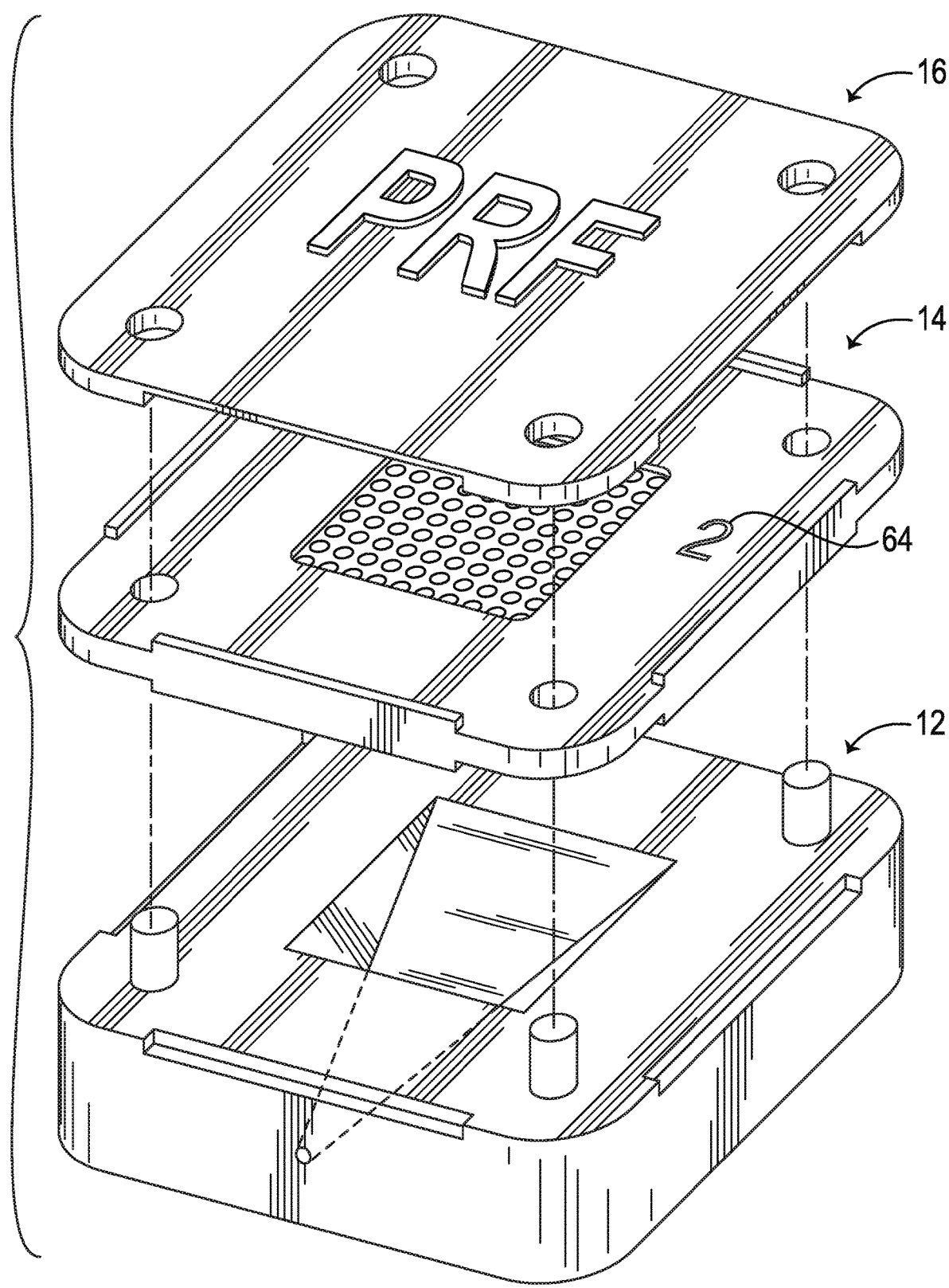
FIG. 1 is a separated view of one embodiment of a tray for processing platelet rich fibrin, illustrating a base, screen attachment, and lid of the tray.
Figure 2:
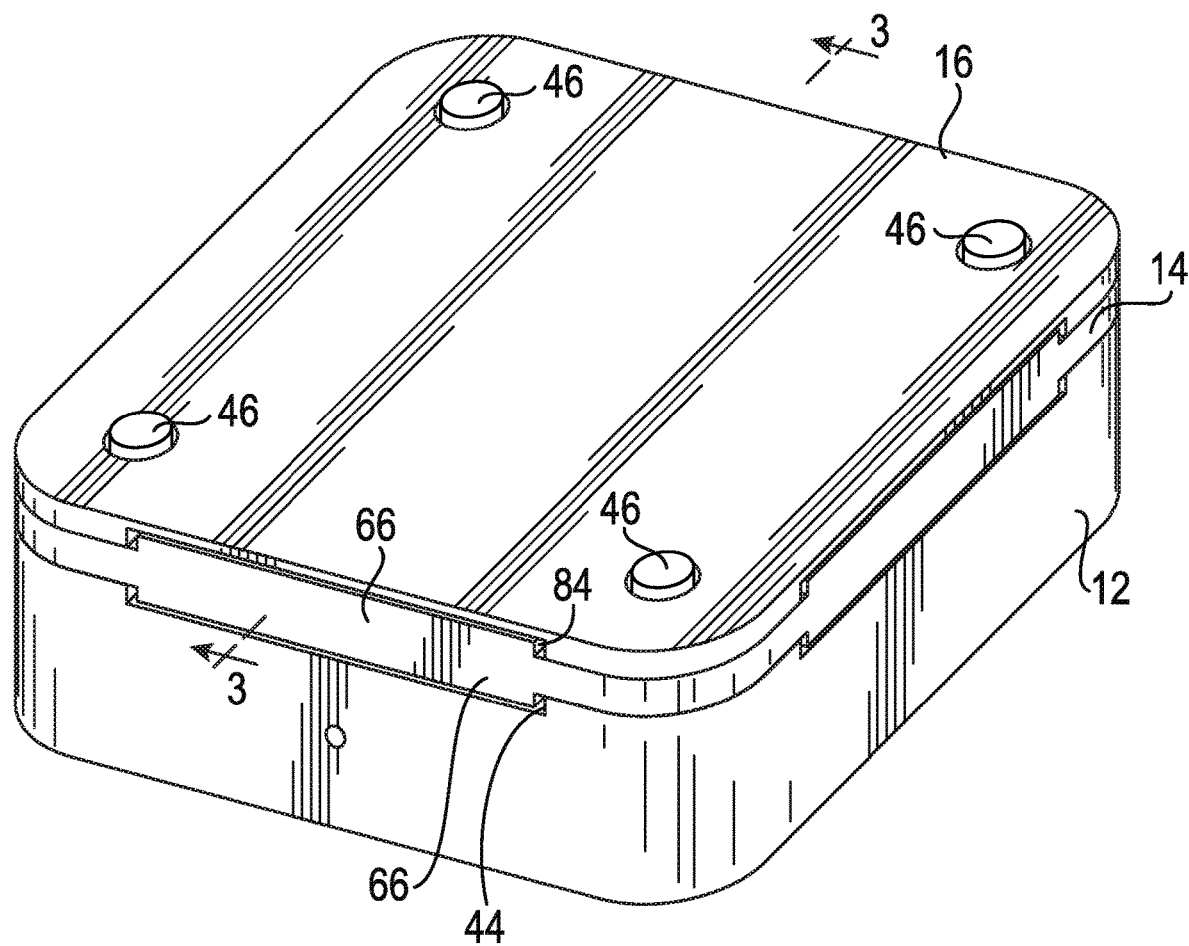
FIG. 2 is a perspective of the tray of FIG. 1, in an assembled position.
Figure 3:
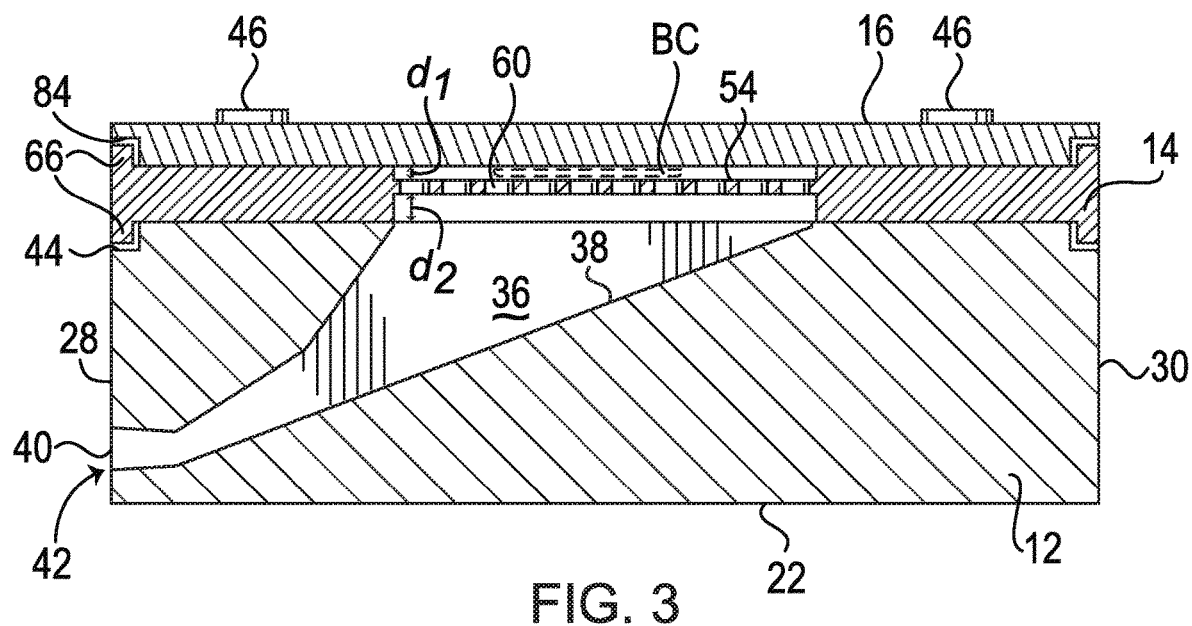
FIG. 3 is a cross section of the assembled tray, illustrating the screen attachment in a first orientation.
Figure 4:
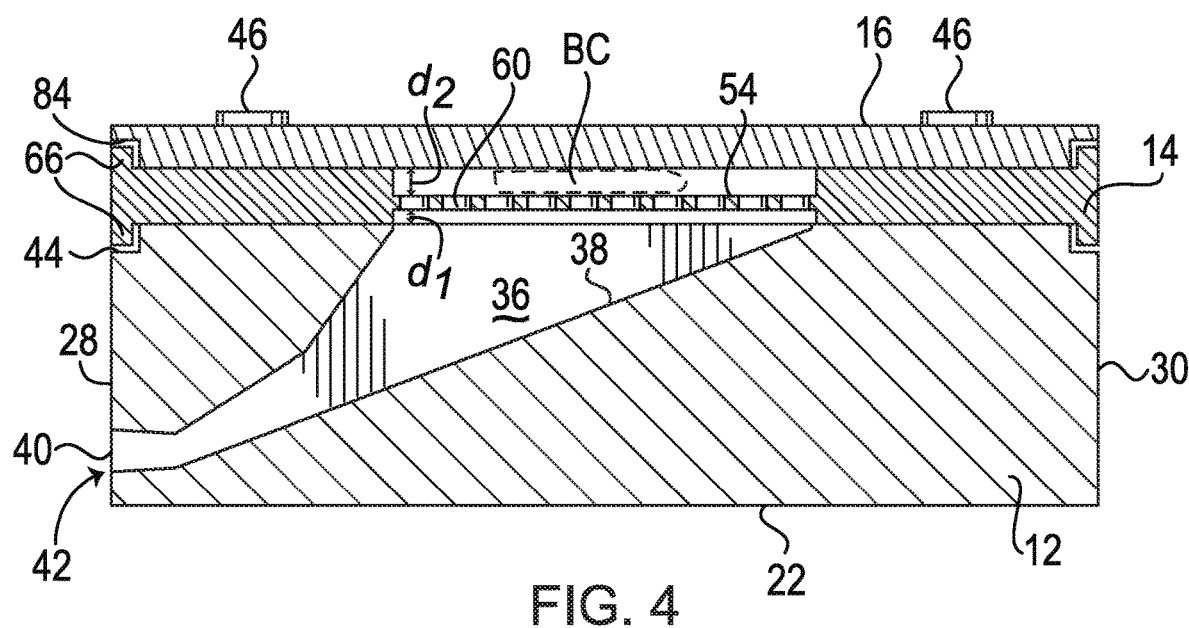
FIG. 4 is a cross section of the assembled tray, illustrating the screen attachment in a second orientation.

The accompanying Figures and this description depict and describe aspects of apparatuses and methods in accordance with the present disclosure, and features and components thereof. It should also be noted that any references herein to front and back, right and left, top and bottom and upper and lower are intended for convenience of description, not to limit the present invention or its components to any one positional or spatial orientation.

Before any aspects of the disclosure are explained in detail, it will be understood that the disclosure is not limited in its application to the details of construction and the arrangement of components set forth in the following description or illustrated in the following drawings. The disclosure is capable of other aspects and of being practiced or of being carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. All numbers expressing measurements and so forth used in the specification and claims are to be understood as being modified in all instances by the term "about."

Referring to FIGS. 1-4, a tray (broadly, an apparatus or assembly) for processing platelet rich fibrin is shown generally at 10. The tray 10 includes a base 12, a fibrin sizing or screen attachment 14, and a lid or top plate 16. The tray 10 can be made of plastic, or any other suitable material. For example, the tray 10 can be made of a stiff plastic, metal, ceramic, or any other stiff non-toxic material. In one embodiment, the tray 10 is a disposable tray configured for one-time use, although a reusable tray that can be sterilized is within the scope of the present invention. Each of the base 12, the screen attachment 14, and the lid 16 includes at least one alignment structure for positioning the components relative to one another. The tray 10 can be used to prepare platelet rich fibrin, such as to compress a fibrin clot to a predetermined thickness, as described in more detail below.

Figure 5:
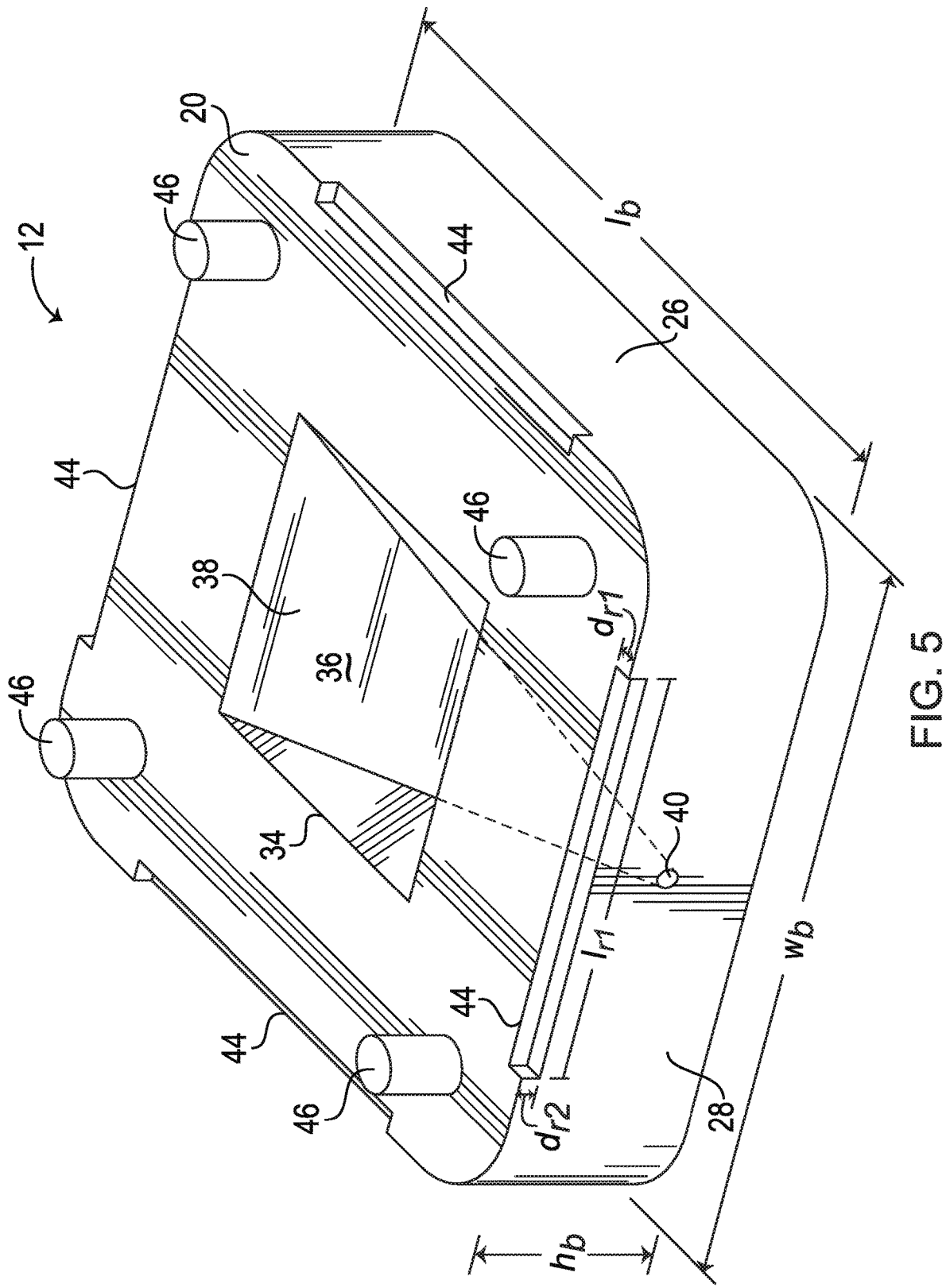
FIG. 5 is a perspective of the base of the tray of FIG. 1.
Figure 6:
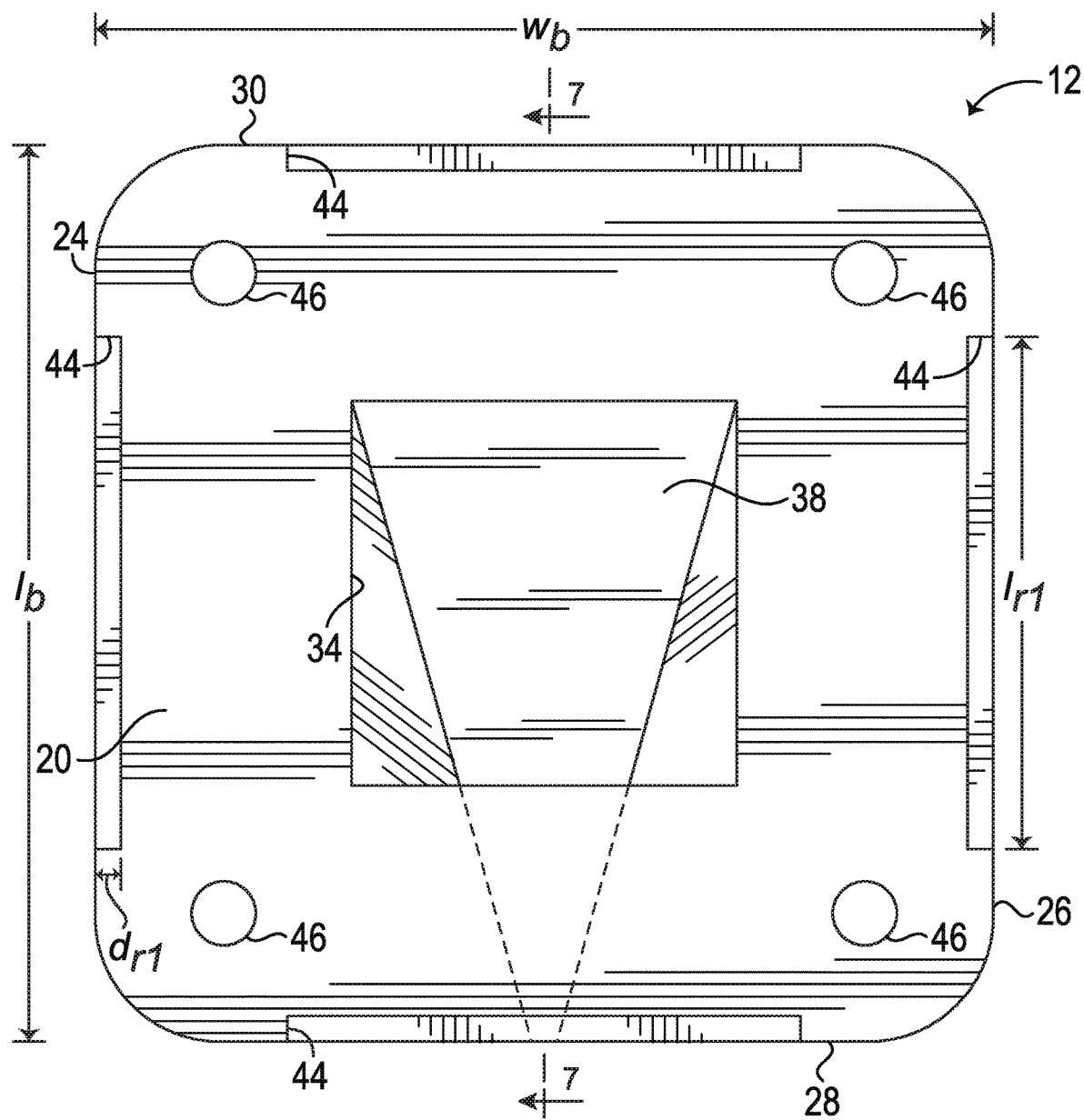
FIG. 6 is a top plan of the base of FIG. 5.
Figure 7:
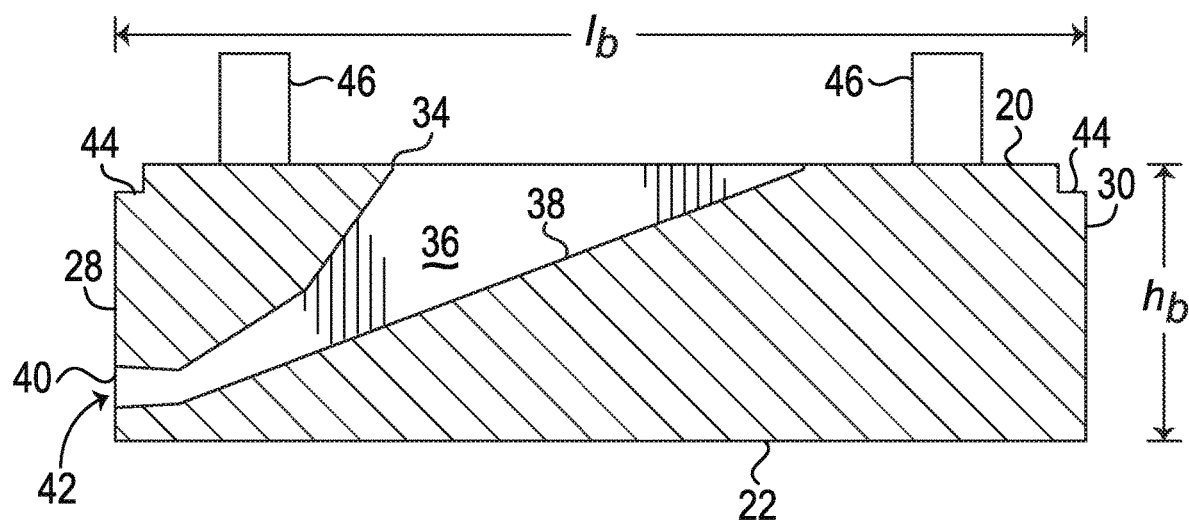
FIG. 7 is a cross section of the base of FIG. 5.

Referring to FIGS. 5-7, the base 12 includes a top surface 20, a bottom surface 22, a left surface 24, a right surface 26, a front surface 28, and a back surface 30. The top and bottom surfaces 20, 22 are substantially horizontal and in spaced parallel arrangement, such that the base 12 has a height $h_b$ extending between the top and bottom surfaces. The left and right surfaces 24, 26 are substantially vertical and extend between the top and bottom surfaces 20, 22 in spaced parallel arrangement, such that the base 12 has a width $w_b$ extending between the left and right surfaces. The front and back surfaces 28, 30 are substantially vertical and extend between the top and bottom surfaces 20, 22 in spaced parallel arrangement, such that the base 12 has a length $l_b$ extending between the front and back surfaces. The height $h_b$ of the base 12 can be in the range of about 10 mm to about 70 mm, although in other embodiments the height $h_b$ can fall outside this range without affecting the utility of the tray 10. In one embodiment, the height $h_b$ of the base 12 is about 20 mm. The width $w_b$ of the base 12 can be in the range of about 40 mm to about 120 mm, or any suitable size to facilitate ease of handling and accommodate creating a platelet rich fibrin the size of common wounds. In one embodiment, the width $w_b$ of the base 12 is about 70 mm. The length $l_b$ of the base 12 can be in the range of about 40 mm to about 120 mm, or any suitable size to facilitate ease of handling and accommodate creating a platelet rich fibrin the size of common wounds. In one embodiment, the length $l_b$ of the base 12 is about 70 mm. In the illustrated embodiment, the length $l_b$ and the width $w_b$ of the base 12 are substantially equal, such that the base is substantially square in shape. However, it is understood that the length $l_b$ and the width $w_b$ of the base 12 need not be substantially equal within the scope of the present invention. The corners of the base 12 can be rounded. For example, in one embodiment, each of the corners has a radius of about 10 mm. The corners of the base 12 can have a different radius, or may not be rounded at all within the scope of the present invention. Other configurations are within the scope of the present invention, such as a rectangular base or other shape base, with or without rounded corners.

As illustrated in FIGS. 5-7, an opening 34 is defined in the top surface 20 of the base 12. In the illustrated embodiment, the opening 34 is centrally located in the top surface 20. The opening 34 may be generally square, or may have other configurations. In one embodiment, the opening 34 is generally square, with sides having a length of about 30 mm. The opening 34 provides access to an interior receptacle 36 (see FIG. 7). A bottom surface 38 of the receptacle 36 is generally slanted downward from a back edge of the opening 34 to the front surface 28 of the base 12. In other words, the base 12 includes a ramp extending from the central opening 34 to the front surface 28. The front surface 28 includes an access opening 40 providing access to contents in the interior receptacle 36. It is understood that the access opening can be in any surface of the base 12, and need not be in the front surface 28. The interior receptacle 36 tapers toward the access opening 40. Contents entering the base 12 through the opening 34 in the top surface 20 will flow downward along the bottom surface or ramp 38 under the force of gravity toward the access opening 40, as will be described in further detail below. The access opening 40 may be configured to permit attachment of a syringe (e.g., a female luer syringe) or other container for removing contents from the base 12. In one embodiment, the access opening 40 comprises a luer connection 42 (e.g., a female luer connection, as illustrated in FIG. 7) to facilitate attachment of a syringe to the base 12 for extraction of contents in the receptacle 36. In one embodiment, the luer connection 42 may extend into the base 12 approximately 8 mm with approximately a 6% taper, such that the luer connection is configured to receive standard syringes, devices with a regular luer, and/or devices with a luer lock. Other configurations are within the scope of the present invention, and it is understood that the access opening need not include a luer connection, and the luer connection can otherwise be configured and dimensioned to receive a standard syringe.

Referring to FIGS. 5 and 6, the base 12 includes positioning recesses 44 configured to accurately position the screen attachment 14 on the base. In the illustrated embodiment, the base 12 includes four recesses 44: one at each edge between the top surface 20 and the left, right, front, and back surfaces 24, 26, 28, 30. Each recess 44 extends a first distance $d_{r1}$ into the top surface and a second distance $d_{r2}$ into the respective left, right, front, or back surface. In one embodiment, each recess 44 extends a distance $d_{r1}$ in the range about 1 mm to about 5 mm into the top surface, such as approximately 2 mm. In one embodiment, each recess 44 extends a distance $d_{r2}$ in the range of 1 mm to about 5 mm into the respective side or end surface, such as approximately 2 mm. Each recess 44 can extend any suitable distance $d_{r1}$ and distance $d_{r2}$ into the respective surfaces so as to permit the screen attachment 14 to easily fit into the recess (as described below) without permitting the screen attachment to loosely slide around within the recess. In the illustrated embodiment, each recess 44 extends an equal distance into both the top surface and the respective side or end surface (e.g., 2 mm), although other configurations are within the scope of the present invention. For example, the distance $d_{r1}$ may be different from the distance $d_{r2}$. As illustrated, each recess 44 has a length $l_{r1}$. The length $l_{r2}$ can be in the range of about 30 mm to about 60 mm, such as about 40 mm. The length $l_{r1}$ can be any suitable length so as to permit the screen attachment 14 to easily fit into the recess (as described below) without permitting the screen attachment to loosely slide around within the recess. Preferably, each recess 44 is centered along the respective edge. It is understood that other configurations are within the scope of the present invention. For example, the base 12 can include fewer than four recesses (e.g., two recesses, on adjacent or opposite edges; see FIG. 13), or more than four recesses (e.g., multiple recesses along one or more edges). The recesses need not be substantially identically sized and positioned, but can vary in size, position, and/or shape to require a specific orientation of the screen attachment 14 on the base 12. In the illustrated embodiment, the recesses 44 are substantially identical in size (e.g., length and distance into adjacent surfaces), position (e.g., centered along the edge), and shape (e.g., generally rectangular), such that the screen attachment 14 can be placed on the base 12 in any orientation, as described in further detail below.

Referring still to FIGS. 5 and 6, the base 12 further includes posts 46 projecting upward from the top surface 20 of the base. The posts 46 are positioned and configured to accurately align the screen attachment 14 and the lid 16 on the base 12. In the illustrated embodiment, the base 12 includes four posts 46, each positioned generally adjacent a corner of the top surface 20. As illustrated, the posts 46 can be generally cylindrical, although other shapes are within the scope of the present invention. In one embodiment, each post 46 is generally cylindrical and has a diameter in a range of about 1 mm to about 10 mm, such as about 5 mm. The diameter can be any suitable size so as to prevent or reduce the likelihood of breaking while occupying minimal space on the base 12. In one embodiment, each post 46 has a height in a range of about 4 mm to about 20 mm, such as about 8 mm. The posts can have any suitable height so as to permit alignment with the screen attachment 14 and the lid 16 when a fibrin clot is on the screen attachment, as described below, while avoiding being overly large and cumbersome. In one embodiment, each post 46 has a minimum height of 8 mm. In one embodiment, each post 46 has a diameter of about 5 mm and extends a height of about 8 mm above the top surface 20. Each post 46 can be spaced inward from the adjacent side and end edges by a distance of about 10 mm to the center of the post, although other configurations and spacing are possible. It is understood that other configurations are within the scope of the present invention. For example, the base 12 can include fewer than four posts, or more than four posts. The posts need not be substantially identically sized and positioned, but can vary in size, position, and/or shape to require a specific orientation of the screen attachment 14 and the lid 16 on the base 12. In the illustrated embodiment, the posts 46 are substantially identical in size (e.g., height and diameter), position (e.g., distance from edges), and shape (e.g., cylindrical), such that the screen attachment 14 and lid 16 can be placed on the base 12 in any orientation, as described in further detail below.

Figure 8:
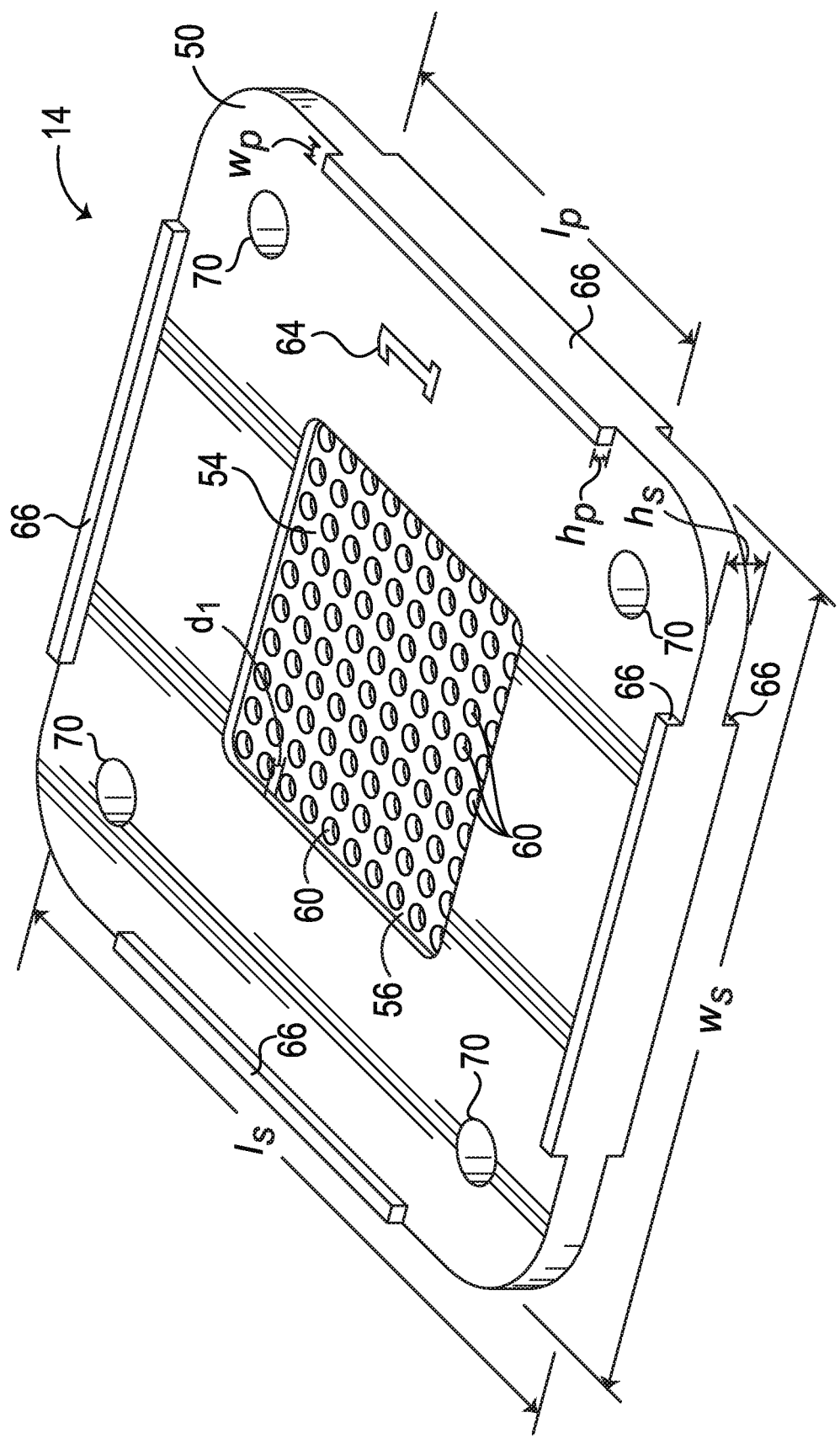
FIG. 8 is a perspective of the screen attachment of the tray of FIG. 1.
Figure 9:
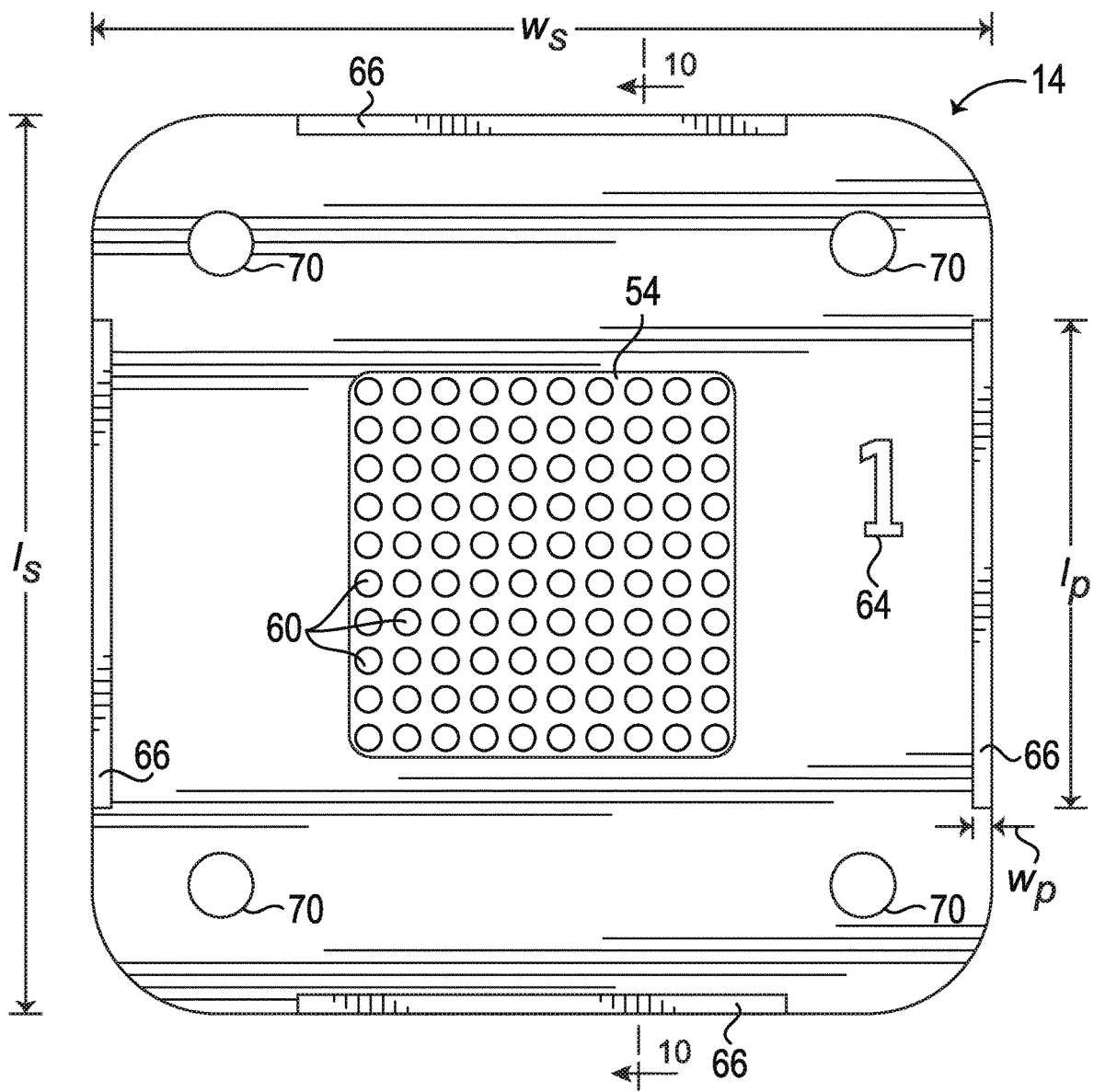
FIG. 9 is a top plan of the screen attachment of FIG. 8.
Figure 10:
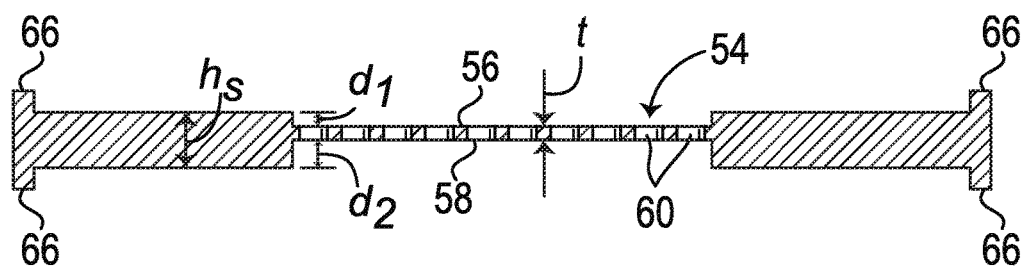
FIG. 10 is a cross section of the screen attachment of FIG. 8.

Referring now to FIGS. 8-10, the screen attachment 14 includes a top surface 50 and a bottom surface 52. The top and bottom surfaces 50, 52 are substantially horizontal and in spaced parallel arrangement, such that the screen attachment 14 has a height $h_s$ extending between the top and bottom surfaces. The screen attachment 14 has a width $w_s$ and a length $l_s$. The height $h_s$ of the screen attachment 14 can be in the range of about 1 mm to about 10 mm. The height $h_s$ of the screen attachment 14 can be any suitable size such that the screen attachment is neither too flimsy nor too cumbersome. In one embodiment, the height $h_s$ of the screen attachment 14 is about 4 mm. The width $w_s$ of the screen attachment 14 can be in the range of about 40 mm to about 120 mm, in the range of about 20 mm to about 100 mm, or any suitable size to facilitate ease of handling and accommodate creating a platelet rich fibrin the size of common wounds. In one embodiment, the width $w_s$ of the screen attachment is about 70 mm. The length $l_s$ of the screen attachment 14 can be in the range of about 40 mm to about 120 mm, in the range of about 20 mm to about 100 mm, or any suitable size to facilitate ease of handling and accommodate creating a platelet rich fibrin the size of common wounds. In one embodiment, the length $l_s$ of the screen attachment 14 is about 70 mm. In the illustrated embodiment, the screen attachment 14 is generally square, such that the width $w_s$ is substantially equal to the length $l_s$, although other shapes and configurations are within the scope of the present invention. Preferably, the screen attachment 14 has the same shape as the base 12. As illustrated, the width $w_s$ of the screen attachment 14 is equal to the width $w_b$ of the base 12, and the length $l_s$ of the screen attachment is equal to the length $l_b$ of the base, although other configurations are within the scope of the present invention. The corners of the screen attachment 14 can be rounded. For example, in one embodiment, each of the corners has a radius of about 10 mm. Other configurations are within the scope of the present invention, such as a rectangular screen attachment, with or without rounded corners, or a screen attachment that does not have the same shape as the base.

As illustrated in FIGS. 8-10, the screen attachment 14 includes a screen 54. The screen 54 is configured and positioned to overlie the opening 34 of the base 12 when the screen attachment 14 is attached to the base. In one embodiment, the screen 54 is substantially square, although other configurations are within the scope of the present invention. For example, the screen 54 can have a length and a width of approximately 38 mm. Preferably, the screen 54 is centrally positioned, as illustrated. For example, the screen 54 may be positioned about 16 mm from each edge of the top surface 50. As seen in FIG. 10, the screen 54 has a thickness t extending between a top surface 56 of the screen and a bottom surface 58 of the screen. The thickness t can be in the range of about 1 mm to about 5 mm, or any suitable size to ensure the screen is not flimsy and is easy to handle. For example, in one embodiment, the screen 54 has a thickness t of about 1 mm. In another embodiment, the screen 54 has a thickness t of about 2 mm. The screen 54 includes holes 60 to permit the passage of liquid or other substance through the screen. The screen 54 can include any number of holes 60 at any spacing. In one embodiment, the holes extending through the screen 54 have a diameter of about 2 mm. In another embodiment, the holes extending through the screen 54 have a diameter of about 1.5 mm. In one embodiment, the screen 54 includes about 100 holes 60, arranged in a 10 by 10 grid configuration of equally spaced holes. Other hole configurations are within the scope of the present invention. For example, the holes can have any size and be configured in any pattern within the scope of the present invention.

As illustrated, the screen 54 is not coplanar with either the top surface 50 or the bottom surface 52 of the screen attachment 14 (see, e.g., FIG. 10). Rather, both the top and bottom surfaces 56, 58 of the screen 54 are positioned between the top and bottom surfaces 50, 52 of the screen attachment 14, such that the screen 54 is inset in the screen attachment 14. The top surface 56 of the screen 54 is spaced a first distance $d_1$ below the top surface 50 of the screen attachment 14. The bottom surface 58 of the screen 54 is spaced a second distance $d_2$ above the bottom surface 52 of the screen attachment 14. The first distance $d_1$ is different from the second distance $d_1$. In other words, the screen 54 is offset between the top and bottom surfaces 50, 52 of the screen attachment 14. In the illustrated embodiment, the screen 54 is positioned closer to the top surface 50 of the screen attachment (i.e., the distance $d_1$ is smaller than the distance $d_2$). The distances $d_1$ and $d_2$ can each be in a range of about 0.25 mm to about 3 mm. In one embodiment, the distance $d_1$ is about 1 mm. In another embodiment, the distance $d_1$ is about 0.5 mm. In one embodiment, the distance $d_2$ is about 2 mm. The greater of the two distances $d_1$ and $d_2$ ($d_2$ as illustrated) can be greater than the other distance ($d_1$ as illustrated) but less than the diameter of the tube in which the blood was collected. In one embodiment, $d_1$ is about 0.5 mm and $d_2$ is about 2 mm. Optionally, the top and bottom surfaces 50, 52 of the screen attachment 14 include indicia 64 indicating the distance the screen 54 is spaced from the respective surface (see, e.g., FIG. 13). Alternatively, the screen attachment 14 can include indicia otherwise identifying the different sides of the screen, such as indicia indicating which side of the screen should be used first, as described in more detail below. In one embodiment, the screen attachment includes markings indicating size (e.g., ruler markings or indicia) for use in determining the size of a fibrin clot. For example, the screen attachment can include ruler markings 65 (e.g., measurements in centimeters, millimeters, inches, or any suitable unit(s)) on the top surface, the bottom surface, any surface adjacent the screen, and/or any combination thereof (see, for example, FIG. 13). The ruler markings can be used to measure the size of a fibrin clot on one or both sides of the screen, before and/or after the fibrin clot is compressed. For example, a fibrin clot can be measured using the ruler markings and compressed until the ruler markings indicate the fibrin clot is a suitable size for application to a wound that has been measured. In one embodiment, the screen attachment includes markings at regular intervals to accurately measure clot size. It is understood that other configurations are within the scope of the present invention, and that the screen attachment need not include indicia.

Figure 13:
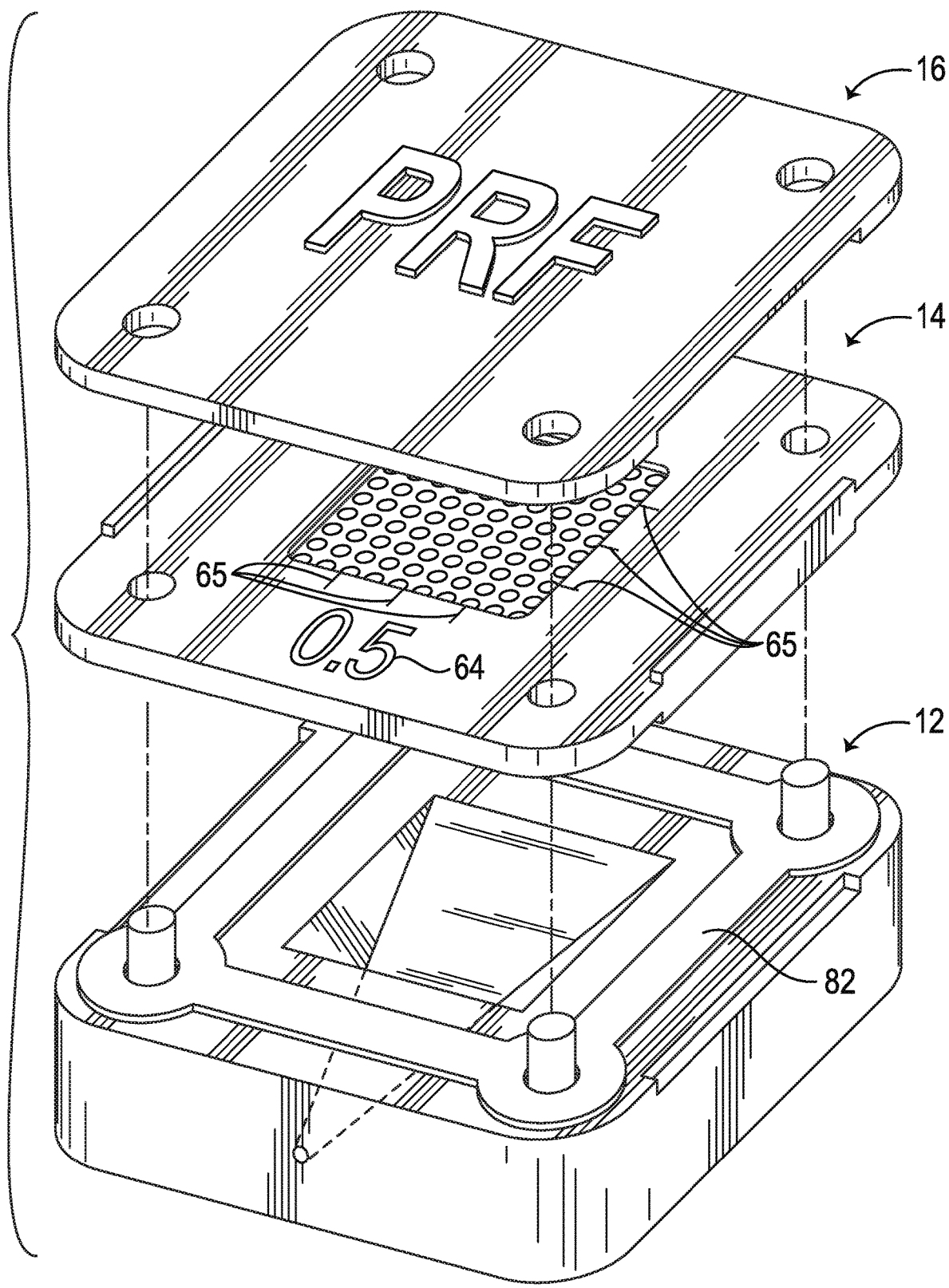
FIG. 13 is separated view of an embodiment of a tray for processing platelet rich fibrin, illustrating a base, screen attachment, and lid of the tray.

Referring to FIGS. 8-10, the screen attachment 14 includes positioning projections 66 configured to accurately position the screen attachment on the base 12. In the illustrated embodiment, the screen attachment 14 includes eight positioning projections 66: one extending upward from each edge of the top surface 50, and one extending downward from each edge of the bottom surface 52. The projections 66 are configured and dimensioned to be received in the recesses 44 on the base 12 to align the screen attachment 14 with the base. The screen attachment 14 is aligned with the base 12 such that the screen 54 overlies the opening 34 of the base. Preferably, each projection 66 is centered along the respective edge. Each projection 66 has a height $h_p$, a length $l_p$, and a width $w_p$. In one embodiment, each projection 66 has a height $h_p$ in the range of about 0.5 mm to about 5 mm, for example about 1.5 mm. Each projection 66 has a height $h_p$ of any suitable size slightly smaller than the distance $d_{r2}$ that the recesses 44 extend into the respective surfaces of the base 12. In one embodiment, each projection 66 has a length $l_p$ in the range of about 28 mm to about 60 mm, for example about 38 mm. Each projection 66 has a length $l_p$ of any suitable size slightly smaller than the length $l_{r1}$ of the recesses 44 of the base 12. In one embodiment, each projection 66 has a width $w_p$ in the range of about 0.5 mm to about 5 mm, for example about 1.5 mm. Each projection 66 has a width $w_p$ of any suitable size slightly smaller than the distance $d_{r1}$ that the recesses 44 extend into the top surface of the base 12. In the illustrated embodiment, the projections 66 are substantially uniform in size, position, and shape, although other configurations are within the scope of the present invention. As illustrated, each projection 66 extending upward away from the top surface 50 is generally aligned with a projection 66 extending downward away from the bottom surface 52. Either the upward or downward extending projections 66 can be received in the recesses 44 of the base. Thus, the screen attachment 14 can be positioned on the base 12 with either the top surface facing upward away from the base or the bottom surface facing upward away from the base. In the illustrated embodiment, the screen attachment 14 is substantially square and the projections 66 and recesses 44 are substantially identical in size, position, and shape, such that the screen attachment can be placed on the base in any orientation. In other words, the screen attachment 14 can be placed on the base with either the top surface 50 or the bottom surface 52 facing up, and with any edge facing the front of the base. When the screen attachment 14 is positioned on the base 12 such that some projections 66 (e.g., four of the projections) are received in the recesses 44 of the base, the lowermost surface of the top surface 50 and the bottom surface 52 is positioned flush against the top surface 20 of the base. It is understood that other configurations are within the scope of the present invention. For example, the screen attachment can include fewer or more projections, depending on the corresponding configuration of the base. See, for example, FIG. 13, illustrating projections on two opposite sides of the screen attachment.

Referring still to FIGS. 8-10, the screen attachment further includes post openings 70. The post openings 70 are positioned and configured to receive the posts 46 of the base 12 to accurately align the screen attachment 14 on the base. In the illustrated embodiment, the screen attachment 14 includes four post openings 70, each positioned generally adjacent a corner of the screen attachment. As illustrated, the openings 70 can be generally circular, although other shapes are within the scope of the present invention. In one embodiment, each opening 70 is generally circular and has a diameter that is equal to or greater than the diameter of the corresponding post 46. For example, in one embodiment, each post opening 70 has a diameter in a range of about 2 mm to about 10 mm, such as about 6 mm. Each post opening 70 has a diameter suitable to permit a post 46 of the base 12 to easily fit into the post opening without permitting the post to loosely slide around in the post opening. In one embodiment, each post opening 70 can be spaced inward from the adjacent side and end edges by a distance of about 10 mm to the center of the post opening. It is understood that other configurations are within the scope of the present invention. The post openings need not be substantially identically sized and positioned, but can vary in size, position, and/or shape to require a specific orientation of the screen attachment 14 on the base 12. In the illustrated embodiment, the post openings are substantially identical in size (e.g., diameter), position (e.g., distance from edges), and shape (e.g., circular), such that the screen attachment 14 can be placed on the base 12 in any orientation, as described above.

Figure 11:
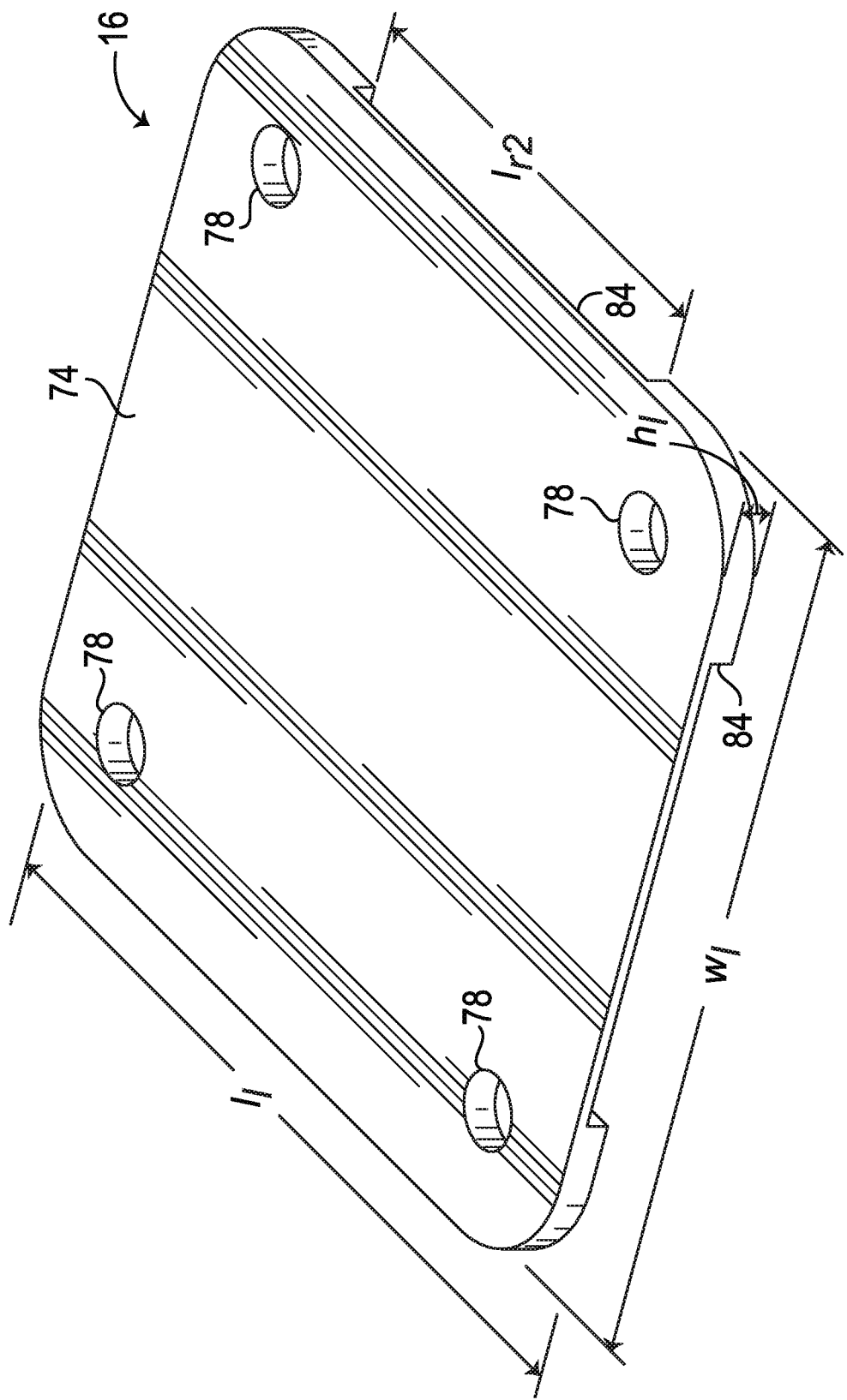
FIG. 11 is a top perspective of the lid of the tray of FIG. 1.
Figure 12:
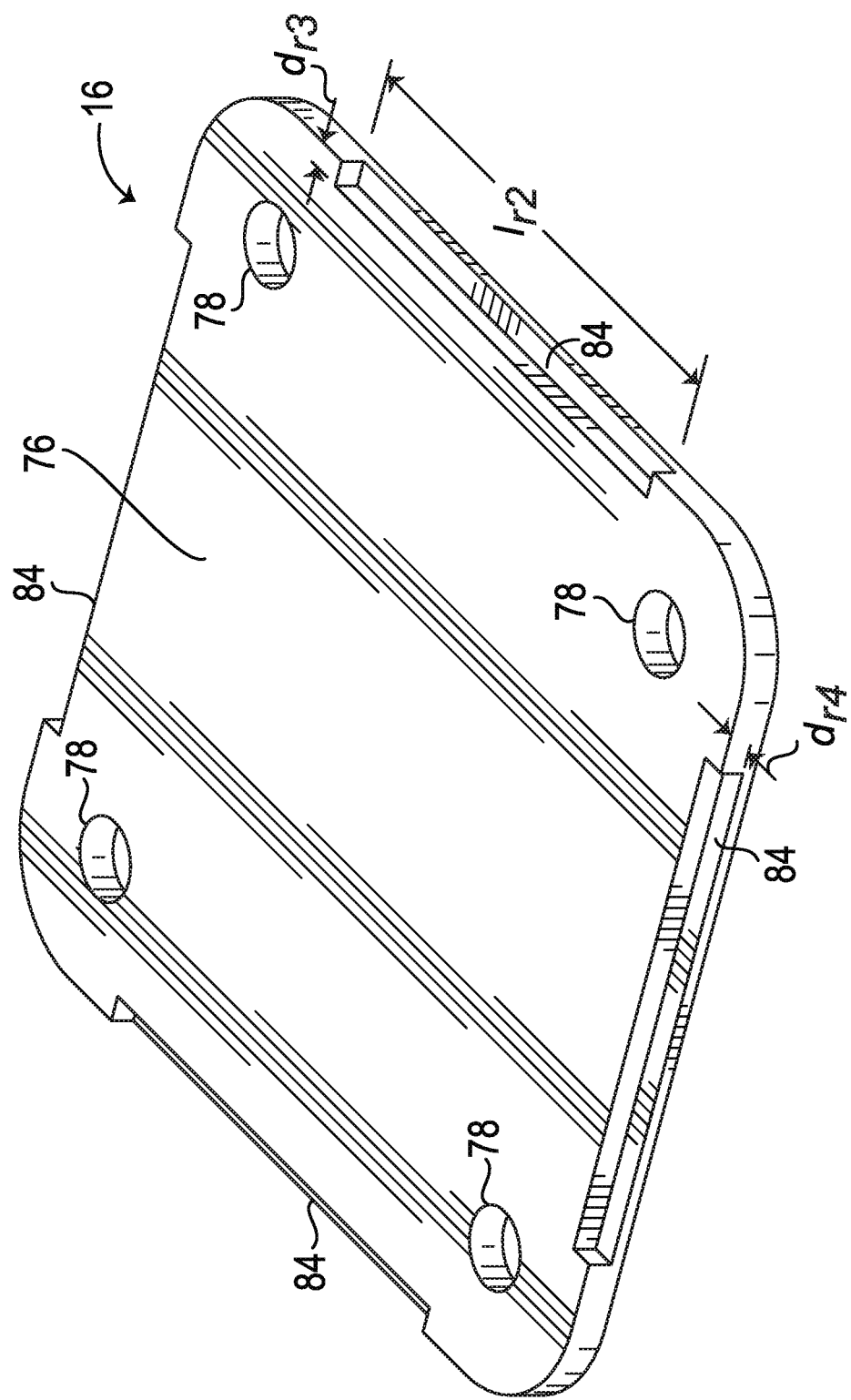
FIG. 12 is a bottom perspective of the lid of FIG. 11.

Referring now to FIGS. 11 and 12, the lid 16 is generally planar and has a top surface 74 and a bottom surface 76. The top and bottom surfaces 74, 76 are substantially horizontal and in spaced parallel arrangement, such that the lid has a height $h_l$ extending between the top and bottom surfaces. The lid 16 has a width $w_l$ and a length $l_l$. The height $h_l$ of the lid 16 can be in the range of about 2 mm to about 10 mm, or any suitable size to prevent flimsiness while providing easy handling. In one embodiment, the height $h_l$ of the lid 16 is about 3 mm. The width $w_l$ of the lid 16 can be in the range of about 40 mm to about 120 mm, or any suitable size to facilitate ease of handling and accommodate creating a platelet rich fibrin the size of common wounds. In one embodiment, the width $w_l$ of the lid 16 is about 70 mm. The length $l_l$ of the lid 16 can be in the range of about 40 mm to about 120 mm, or any suitable size to facilitate ease of handling and accommodate creating a platelet rich fibrin the size of common wounds. In one embodiment, the length $l_l$ of the lid 16 is about 70 mm. In the illustrated embodiment, the lid 16 is generally square, such that the width $w_1$ is substantially equal to the length $l_l$. Preferably, the lid 16 has the same shape as the base 12. As illustrated, the width $w_1$ of the lid 16 is equal to the width $w_s$ of the screen attachment 14 and the width $w_b$ of the base 12, and the length $w_l$ of lid is equal to the length $l_s$ of the screen attachment and the length $l_b$ of the base, although other configurations are within the scope of the present invention. The corners of the lid 16 can be rounded. For example, in one embodiment, each of the corners has a radius of about 10 mm. Other configurations are within the scope of the present invention, such as a rectangular lid, with or without rounded corners, or a lid that does not have the same shape as the base.

The lid 16 includes positioning recesses 84 configured to accurately position the lid on the screen attachment 14 (e.g., when the screen attachment is positioned on the base 12). In the illustrated embodiment, the lid 16 includes four recesses 84: one at each edge between the bottom surface 76 and the left, right, front, and back surfaces of the lid. Each recess 84 extends a first distance $d_{r3}$ into the bottom surface and a second distance $d_{r4}$ into the respective left, right, front, or back surface. In one embodiment, each recess 84 extends a distance $d_{r3}$ in the range about 1 mm to about 5 mm into the bottom surface, such as approximately 2 mm. In one embodiment, each recess 84 extends a distance $d_{r4}$ in the range of 1 mm to about 5 mm into the respective side or end surface, such as approximately 2 mm. Each recess 84 can extend any suitable distance $d_{r1}$ and distance $d_{r2}$ into the respective surfaces so as to permit projections 66 of the screen attachment 14 to easily fit into the recess without permitting the screen attachment to loosely slide around within the recess. In the illustrated embodiment, each recess 84 extends an equal distance into both the bottom surface and the respective side or end surface (e.g., 2 mm), although other configurations are within the scope of the present invention. For example, the distance $d_{r3}$ may be different from the distance $d_{r1}$. As illustrated, each recess 84 has a length $l_{r2}$. The length $l_{r2}$ can be in the range of about 30 mm to about 60 mm, such as about 40 mm. The length $l_{r2}$ can be any suitable length so as to permit the screen attachment 14 to easily fit into the recess without permitting the screen attachment to loosely slide around within the recess. Preferably, each recess 84 is centered along the respective edge. It is understood that other configurations are within the scope of the present invention. For example, the lid 16 can include fewer than four recesses (e.g., two recesses, on adjacent or opposite edges; see FIG. 13), or more than four recesses (e.g., multiple recesses along one or more edges). The recesses need not be substantially identically sized and positioned, but can vary in size, position, and/or shape to require a specific orientation of the screen attachment 14. In the illustrated embodiment, the recesses 84 are substantially identical in size (e.g., length and distance into adjacent surfaces), position (e.g., centered along the edge), and shape (e.g., generally rectangular), such that the lid 16 can be placed on the screen attachment 14 in any orientation. Preferably, as illustrated, the recesses 84 have the same size, position, and shape as the recesses 44 of the base, such that each set of recesses can receive the projections 66 of the screen attachment 14 in any orientation. However, other configurations are within the scope of the present invention.

Referring still to FIGS. 11 and 12, the lid 16 further includes post openings 78. The post openings 78 are positioned and configured to receive the posts 46 of the base 12 to accurately align the lid 16 on the base. In the illustrated embodiment, the lid 16 includes four post openings 78, each positioned generally adjacent a corner of the lid. As illustrated, the openings 78 can be generally circular, although other shapes are within the scope of the present invention. In one embodiment, each opening 78 is generally circular and has a diameter that is equal to or greater than the diameter of the corresponding post 46. For example, in one embodiment, each post opening 78 has a diameter in a range of about 2 mm to about 10 mm, such as about 6 mm. Each post opening 78 has a diameter suitable to permit a post 46 of the base 12 to easily fit into the post opening without permitting the post to loosely slide around in the post opening. In one embodiment, each post opening 78 can be spaced inward from the adjacent side and end edges by a distance of about 10 mm to the center of the post opening. When the lid 16 is positioned on the screen attachment 14 and the base 12 such that the posts 46 extend through both the post openings 70 and the post openings 78, the bottom surface of the lid is flush with the uppermost surface of the screen attachment 14 (whether the screen attachment is oriented so that the top surface 50 or the bottom surface 52 is the uppermost surface). It is understood that other configurations are within the scope of the present invention. The post openings need not be substantially identically sized and positioned, but can vary in size, position, and/or shape to require a specific orientation of the lid 16 on the base 12. In the illustrated embodiment, the post openings are substantially identical in size (e.g., diameter), position (e.g., distance from edges), and shape (e.g., circular).

Figure 14:
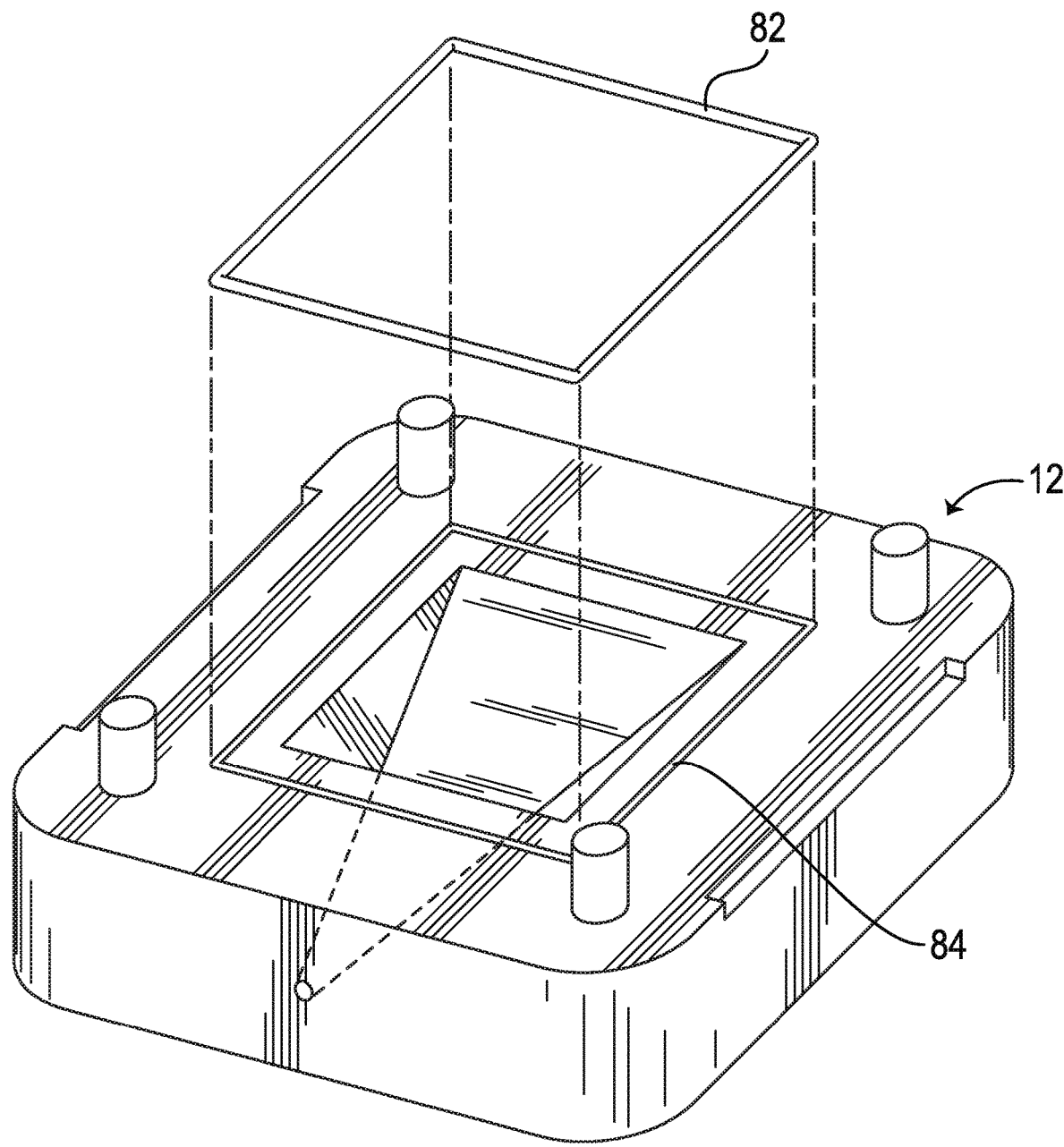
FIG. 14 is a perspective of an embodiment of a base, illustrating a sealing member for sealing between the base and the screen attachment.

Optionally, the tray assembly 10 can also include a sealing member 82 positioned between the base 12 and the screen attachment 14. The sealing member 82 can be made of any suitable soft, rubber-like material (e.g., silicone, material having a Shore A hardness of about 10, or any other suitable sealing material). Preferably, the sealing member is made of latex-free, non-toxic, hypo-allergenic material. When the tray 10 is assembled for use, the sealing member 82 engages the base 12 and the surface of the screen attachment 14 adjacent the base (e.g., the top surface 50 or the bottom surface 52, depending on the orientation of the screen attachment) to seal therebetween. Preferably, the sealing member 82 does not interfere with the positioning recesses 44, the screen 54, or the positioning projections 66. The sealing member 82 provides an air-tight seal between the base 12 and the screen attachment 14. This ensures that when fluid is removed from the tray 10 through the access opening, no air is drawn through any gap between the screen attachment and the base. In other words, the sealing member 82 ensures fluid is aspirated correctly. As illustrated in FIG. 13, in one embodiment the sealing member 82 comprises a gasket configured for attachment to the base 12. For example, the gasket can include openings configured to receive the posts 46 to attach the gasket to the base 12. The gasket can be any suitable size configured to seal between the base 12 and the screen attachment 14. In one embodiment, the gasket is about 4 mm wide and about 1.5 mm thick, with holes having diameters of about 6 mm to receive the posts 46. Other dimensions and configurations are within the scope of the invention. In another embodiment, illustrated in FIG. 14, the base includes a groove 84 surrounding the opening 34. In this embodiment, the sealing member 82 comprises an O-ring type sealing member configured to be received in the groove 84 for attachment to the base 12, while extending out of the groove above the base to seal between the base and the screen attachment 14. It is understood that any configuration of a seal between the base 12 and the screen attachment 14 is within the scope of the present invention, or the sealing member can be omitted within the scope of the present invention.

Referring now to FIGS. 1-4, use of the tray 10 to process platelet rich fibrin will be explained. First, the screen attachment 14 is placed on the base 12 such that recesses 44 receive projections 66, post openings 70 receive posts 46, and the screen 54 overlies the opening 34. Then, a fibrin clot BC is placed on the screen 54 of the screen attachment 14. The lid 16 is placed on the base 12 on top of the screen attachment 14 such that the post openings 78 receive posts 46. The lid 16 is pressed downward to compress the fibrin clot BC on the screen 54. As the fibrin clot BC is compressed, serum is expressed from the clot, goes through the holes 60 in the screen 54, and flows into the interior receptacle 36 of the base 12 through the opening 34. The tapered receptacle 36, including the slanted bottom surface 38, directs the serum in the receptacle 36 toward the access opening 40, where, for example, a syringe collects the serum. The lid 16 is pressed downward until it is flush against the uppermost major surface of the screen attachment 14. The fibrin clot BC is compressed to a thickness equal to the distance between the screen 54 and the lid 16, thereby forming a compressed layer of platelet rich fibrin having a consistent thickness. Because the lid 16 is pressed downward until it is flush with the screen attachment 14, and the screen 54 is positioned below the surface of the screen attachment by a distance (e.g., $d_1$), the fibrin clot BC is compressed to a thickness substantially equal to the distance between the screen and the surface of the screen attachment. The serum can be removed from the interior receptacle 36 (e.g., by connecting a syringe to the luer connection 42) and used in a medical procedure (e.g., injected into a wound to aid healing). The compressed platelet rich fibrin can be removed from the screen 54 and used in a medical procedure (e.g., placed over a wound to aid healing).

As described above, the screen attachment 14 can be placed in any orientation on the base 12. Because the screen 54 is offset between the top and bottom surfaces 50, 52 of the screen attachment 14, the tray 10 can be used to compress a fibrin clot BC to a first thickness, and then further compress the fibrin clot to a second thickness smaller than the first thickness. For example, the screen attachment 14 can be placed on the base 12 as described above in a first orientation with a first surface (e.g., the bottom surface 52) facing upward away from the base. The fibrin clot BC can be compressed as described above to express serum and form a compressed platelet rich fibrin clot having a first thickness equal to a first distance between the screen 54 and the lid 16 (e.g., 2 mm). The screen attachment 14 can then be flipped, such that a second surface (e.g., the top surface 50) is facing upward away from the base 12. The compressed platelet rich fibrin is placed on the screen and compressed again to a second thickness equal to a second distance between the screen 54 and the lid 16 and smaller than the first thickness (e.g., 0.5 mm). Optionally, multiple clots can be placed on the screen 54 with portions overlapping, and the subsequent compression of the clots to the uniform thickness using the tray 10 will form one larger clot from the multiple clots. The compressed clot can then be used in a medical procedure, such as by placing the clot over a wound or suturing the clot onto or into a wound to aid healing. In one embodiment, multiple clots are placed on the screen 54 without any portions overlapping and the clots are compressed to a first thickness as described above. Subsequently, the screen attachment 14 can be flipped, and the multiple compressed clots can be placed on the screen 54 with portions overlapping such that the second additional compression forms one larger clot from the multiple clots, the one larger clot having a second thickness smaller than the first thickness.

The tray 10 as shown and described allows a user to simultaneously collect serum and shape fibrin for use in medical procedures. As described above, the tapered ramp in the base 12 directs fluid flowing through the screen 54 and into the opening 34 of the base toward an access opening 40, where it can be extracted for use in a medical procedure. As discussed above, the screen attachment 14 includes a screen 54 offset between the top and bottom surfaces 50, 52 of the screen attachment. Thus, the tray 10, specifically the screen attachment 14 of the tray, can be used in a first orientation to compress a clot to a first thickness, and used in a second orientation to compress a clot to a second thickness different from the first thickness.

It will be understood that various features of the aspects of the apparatus and methods described herein may be used in combination with, or instead of, particular features of another aspect. Having provided the disclosure in detail, it will be apparent that modifications and variations are possible without departing the scope of the disclosure defined in the appended claims. Furthermore, it should be appreciated that all examples in the present disclosure are provided as non-limiting examples.

What is claimed is:

1. A tray for processing platelet rich fibrin, the tray comprising:
a base having top, bottom, left, right, front, and back surfaces, the base including at least one alignment structure;
a screen attachment having a top surface, a bottom surface, and a screen inset between the top and bottom surfaces, the screen attachment having at least one alignment structure configured for engagement with the at least one alignment structure of the base to align the screen attachment with the base; and
a lid having a top surface, a bottom surface, and at least one alignment structure configured for engagement with the at least one alignment structure of the base to align the lid with the screen attachment and the base,
wherein the screen is spaced a first distance below the top surface of the screen attachment and spaced a second distance different from the first distance above the bottom surface of the screen attachment, such that when the screen attachment is placed on the base with the top surface facing upward the lid is configured to compress a fibrin clot placed on the screen to a first thickness, and when the screen attachment is placed on the base with the bottom surface facing upward the lid is configured to compress a fibrin clot placed on the screen to a second thickness different from the first thickness
wherein: the at least one alignment structure of the base comprises a recess, and the at least one alignment structure of the screen attachment comprise a projection configured to be received in the recess.

2. The tray as recited in claim 1, wherein
the base further comprises a post, and the screen attachment further comprises a post opening configured to receive the post, and the at least one alignment structure of the lid comprises a post opening configured to receive the post.

3. The tray as recited in claim 1, wherein
the at least one alignment structure of the base and the at least one alignment structure of the screen attachment are configured to permit attachment of the screen attachment to the base in a first orientation where a bottom surface of the screen attachment is oriented downwards towards the base, and in a second orientation where the top surface of the screen attachment is oriented downwards towards the base.

4. The tray as recited in claim 1, wherein
the base further comprises at least one post; and
the screen attachment further comprises at least one post opening configured to receive the at least one post of the base.

5. The tray as recited in claim 4, wherein
the at least one alignment structure of the lid comprises at least one post opening configured to receive the at least one post of the base and at least one recess; and
the at least one projection of the screen attachment comprises at least one projection extending upward from the top surface of the screen attachment and at least one projection extending downward from the bottom surface of the screen attachment,
wherein when the base, lid, and screen attachment are attached the projection extending upward is received in the recess of the lid and the projection extending downward is received in the recess of the base.

6. A tray for processing platelet rich fibrin, the tray comprising:
a base having top, bottom, left, right, front, and back surfaces, the base including at least one alignment structure, the base including an interior receptacle and an opening in the top surface providing access to the interior receptacle;
a screen attachment having a top surface, a bottom surface, and a screen, the screen attachment having at least one alignment structure configured for engagement with the at least one alignment structure of the base to align the screen attachment with the base such that the screen overlies the opening of the base; and
a lid having a top surface, a bottom surface, and at least one alignment structure configured for engagement with the at least one alignment structure of the base to align the lid with the screen attachment and the base,
wherein the base includes an access opening, the interior receptacle being tapered and slanted toward the access opening such that liquid flowing through the screen and into the interior receptacle is directed toward the access opening for removal from the base through the access opening; and
wherein: the screen is spaced a first distance below the top surface of the screen attachment and spaced a second distance different from the first distance above the bottom surface of the screen attachment, such that when the screen attachment is placed on the base with the top surface facing upward the lid is configured to compress a fibrin clot placed on the screen to a first thickness, and when the screen attachment is placed on the base with the bottom surface facing upward the lid is configured to compress a fibrin clot placed on the screen to a second thickness different from the first thickness
wherein: the at least one alignment structure of the base comprises a recess, and the at least one alignment structure of the screen attachment comprise a projection configured to be received in the recess.

7. The tray as recited in claim 6, wherein
the access opening is configured to receive a syringe for removal of liquid from the base.

8. The tray as recited in claim 6, wherein
the base further comprises a post, and the screen attachment further comprises a post opening configured to receive the post, and the at least one alignment structure of the lid comprises a post opening configured to receive the post.

9. The tray as recited in claim 6, wherein
the at least one alignment structure of the base and the at least one alignment structure of the screen attachment are configured to permit attachment of the screen attachment to the base in a first orientation where the bottom surface of the screen attachment is oriented downwards towards the base, and in a second orientation where the top surface of the screen attachment is oriented downwards towards the base.

10. The tray as recited in claim 6, wherein
the base further comprises at least one post; and
the screen attachment further comprises at least one post opening configured to receive the at least one post of the base.

11. The tray as recited in claim 6, wherein
the base further comprises a post, and the screen attachment further comprises a post opening configured to receive the post, and the at least one alignment structure of the lid comprises a post opening configured to receive the post.

12. The tray for processing platelet rich fibrin as set forth in claim 1, wherein:
the fibrin clot is comprised of multiple fibrin clots placed on the screen with portions overlapping and compressed into one larger fibrin clot.

13. The tray for processing platelet rich fibrin, as set forth in claim 6, wherein:
the fibrin clot is comprised of multiple fibrin clots placed on the screen with portions overlapping and compressed into one larger fibrin clot.

* * * * *